(12) United States Patent
Crooks et al.

(10) Patent No.: US 7,226,949 B2
(45) Date of Patent: Jun. 5, 2007

(54) COMPOUNDS OF USE IN THE TREATMENT OF EPILEPSY, SEIZURE, AND ELECTROCONVULSIVE DISORDERS

(75) Inventors: Peter A. Crooks, Nicholasville, KY (US); Aimee Karis Bence, Indianapolis, IN (US); David Robert Worthern, Lexington, KY (US)

(73) Assignee: University of Kentucky, Lexington, KY (US)

( * ) Notice: Subject to any disclaimer, the term of this patent is extended or adjusted under 35 U.S.C. 154(b) by 131 days.

(21) Appl. No.: 10/845,143

(22) Filed: May 14, 2004

(65) Prior Publication Data

US 2004/0266737 A1    Dec. 30, 2004

Related U.S. Application Data

(62) Division of application No. 10/345,387, filed on Jan. 16, 2003, now abandoned.

(60) Provisional application No. 60/348,366, filed on Jan. 16, 2002.

(51) Int. Cl.
*A61K 31/35* (2006.01)
*C07C 211/51* (2006.01)
*C07C 211/54* (2006.01)
*C07C 211/55* (2006.01)
*C07C 225/22* (2006.01)
*C07C 321/26* (2006.01)

(52) U.S. Cl. ............ 514/648; 514/646; 514/658; 564/330; 564/430; 564/434

(58) Field of Classification Search ............ None
See application file for complete search history.

(56) References Cited

U.S. PATENT DOCUMENTS 4,564,636 A    1/1986    Kaplan
4,772,615 A    9/1988    Pavia
4,816,485 A    3/1989    Satzinger et al.
4,857,662 A    8/1989    Satzinger et al.
4,910,312 A    3/1990    Pavia
4,933,368 A    6/1990    Satzinger et al.

OTHER PUBLICATIONS

Database CAPLUS on STN, Acc. No. 1939:17619, McLeod, Biochemical Journal (1938), 32, p. 1770-4 (abstract).*
Database CAPLUS on STN, Acc. No. 1992:99253, Hamada et al, Epilepsy Research (1991), 10(2-3), p. 93-102 (abstract).*
Database CAPLUS on STN, Acc. No. 1948:10534, Barry et al., "Antitubercular activity of diphenyl ethers and related compounds." Nature (1947), 160, p. 800-1 (abstract).

* cited by examiner

*Primary Examiner*—Brian Davis
(74) *Attorney, Agent, or Firm*—McDermott Will & Emery LLP

(57) ABSTRACT

The present invention provides pharmaceutical preparations and the uses thereof for preventing and/or treating seizures and other electroconvulsive disorders by administering a pharmaceutically effective amount of a therapeutic compound having the following formula (I):

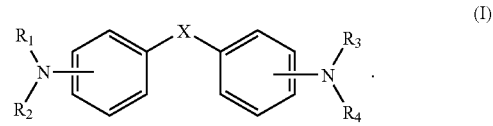

(I)

Embodiments include administering an effective amount of 4,4'-thiodianiline, 4,4'-diaminobenzophenone, 4,4'-methylenedianiline, 4,4'-diaminodiphenyl ether, or (3-aminophenyl)-(4-aminophenyl) amine, an analog, or a pharmaceutically accepted salt or complex thereof to a mammal in need of treatment or prevention of epilepsy, seizure, or other electroconvulsive disorder.

11 Claims, No Drawings

COMPOUNDS OF USE IN THE TREATMENT OF EPILEPSY, SEIZURE, AND ELECTROCONVULSIVE DISORDERS

RELATED APPLICATIONS

This application is a divisional of application Ser. No. 10/345,387 filed Jan. 16, 2003 now abandoned.

This application claims the benefit of U.S. Provisional Patent Application No. 60/348,366 filed Jan. 16, 2002, which is incorporated herein by reference.

FIELD OF THE INVENTION

The present invention relates to bridged dianilino compounds and pharmaceutical compositions and method of use thereof for the prevention and treatment of epilepsies, seizures, and other electroconvulsive disorders. Specifically, this invention relates to the use of 4,4'-thiodianiline, 4,4'-diaminobenzophenone, 4,4'-methylenedianiline, 4,4'-diaminodiphenyl ether, or (3-aminophenyl)-(4-aminophenyl)amine and related compounds, and preparations thereof, for the prevention, palliation and/or treatment of seizures, conduction disturbances and electroconvulsive disorders of all types, manifestations and origins, in humans and in animals.

BACKGROUND OF THE INVENTION

Epilepsy is a general term describing a group of central nervous system disorders that are characterized by recurrent seizures that are the outward manifestation of excessive and/or hyper-synchronous abnormal electrical activity of neurons of the cerebral cortex and other regions of the brain. This abnormal electrical activity can be manifested as motor, convulsion, sensory, autonomic, or psychic symptoms.

Epilepsy affects millions of people worldwide, and over 2.5 million individuals in the United States. For the purposes of clinical assessment, it is useful to classify patients according to the type of seizure the patient experiences. As described in *The Pharmacological Basis of Therapeutics, 9$^{th}$* Ed. (McGraw-Hill) [1], there are two classes of seizures: partial seizures and generalized seizures. Partial seizures consist of focal and local seizures. Partial seizures are further classified as simple partial seizures, complex partial seizures and partial seizures secondarily generalized. Generalized seizures are classified as convulsive and nonconvulsive seizures. They are further classified as absence (previously referred to as 'petit mal') seizures, atypical absence seizures, myoclonic seizures, clonic seizures, tonic seizures, tonic-clonic seizures, and atonic seizures.

Hundreds of epileptic syndromes have been defined as disorders characterized by specific symptoms that include epileptic seizures. These include, but are not limited to, absence epilepsy, psychomotor epilepsy, temporal lobe epilepsy, frontal lobe epilepsy, occipital lobe epilepsy, parietal lobe epilepsy, Lennox-Gastaut syndrome, Rasmussen's encephalitis, childhood absence epilepsy, Ramsay Hunt Syndrome type II, benign epilepsy syndrome, benign infantile encephalopathy, benign neonatal convulsions, early myoclonic encephalopathy, progressive epilepsy and infantile epilepsy. A patient may suffer from any combination of different types of seizures. Partial seizures are the most common, and account for approximately 60% of all seizure types. Regardless of the type of epilepsy, seizures significantly limit the autonomy of the patient.

It is believed that the characteristic seizures of epilepsy are caused by the disordered, synchronous, and rhythmic firing of brain neurons. The neurons can fire at up to four times their normal rate. As a result, epileptic seizures are an overstimulation of the normal neuronal processes that control brain function.

Anti-epileptic drugs are available for treating epilepsies, but these agents have a number of shortcomings. For instance, the agents are often poorly soluble in aqueous and biological fluids or are extremely hygroscopic. Of even greater importance is that patients often become refractory to a drug over time. In addition, many anti-epileptic agents cause unwanted side effects, neurotoxicities, and drug interactions. Even while being treated with one or a combination of the anti-epileptic drugs currently in clinical use, 30% of epileptic patients still experience seizures. As more anti-epileptic drugs are developed, the clinician will have expanded pharmaceutical options when designing an effective treatment protocol for each patient. Accordingly, a continuing need exists for pharmaceutical compositions that treat or prevent epilepsy and its associated symptoms with minimal side effects.

After experimentation and investigation, it has been discovered that oral and intraperitoneal administration of a therapeutic compound comprising formula (I) below to mice and rats resulted in profound and reproducible anticonvulsant or antiepileptic activity in animal modes of seizure disorders. It has further been discovered that these compounds do not show acute neurotoxic effects at the levels required for a therapeutic response.

SUMMARY OF THE INVENTION

An advantage and object of the present invention is a pharmaceutical composition useful for the treatment, prevention and/or amelioration of disorders related to and including epilepsy, seizure, and other electroconvulsive disorders.

According to the present invention, the foregoing objects and advantages are achieved in part by a therapeutic compound, including resolved enantiomers, diastereoisomers, tautomers, salts, solvates and polymorphic forms thereof, having the following formula (I):

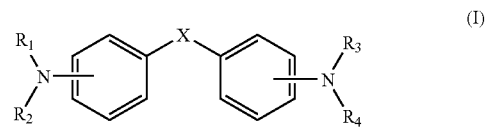

wherein $R_1$, $R_2$, $R_3$, and $R_4$, are each independently selected from the group consisting of hydrogen, hydroxy, amino, phenyl, a substituted or unsubstituted $C_{1-10}$ alkyl, $C_{3-10}$ branched alkyl, a substituted or unsubstituted $C_{3-8}$ cycloalkyl, a substituted or unsubstituted arylalkyl, a substituted or unsubstituted $C_{1-10}$ alkoxyl and a substituted or unsubstituted $C_{1-10}$ acyl; and X is selected from the group consisting of —O—, —S—, —N(H)—, —Se—, —Si—, —CH=CH—, —C≡C—, —N=N—, —N=CH—, —CH=N—, —C(S)—, —N(H)S(O)—, —N(H)SO$_2$—, —N(H)O—, —N(H)S—, —S(O)—, —SO$_2$—, —PO$_4$—, —Si(O)—, —C(O)—, —CH$_2$—, —CF$_2$—, and a covalent bond.

Another object of the present invention is a method of treating, ameliorating, or preventing epilepsy, seizure or electroconvulsive disorders in a subject in need thereof. In an embodiment of the present invention, the method comprises administering an effective amount of 4,4'-thiodianiline, 4,4'-diaminobenzophenone, 4,4'-methylenedianiline, 4,4'-diaminodiphenyl ether, or (3-aminophenyl)-(4-aminophenyl) amine, or a pharmaceutically acceptable salt or complex thereof to a subject in need of treatment, amelioration, or prevention of such disorders.

Further according to the invention, the foregoing objects and advantages for the treatment or prevention of electroconvulsive disorders are achieved by administering a pharmaceutical composition comprising an effective amount of the therapeutic compound to mammals in an admixture with a pharmaceutically acceptable carrier, adjuvant or vehicle.

Still further according to the invention, the foregoing objects and advantages for the treatment or prevention of electroconvulsive disorders are achieved by administering an effective amount of 4,4'-thiodianiline, 4,4'-diaminodiphenyl ether, 4,4'-diaminobenzophenone, 4,4'-methylenedianiline, or (3-aminophenyl)-(4-aminophenyl) amine, or a pharmaceutically acceptable salt or complex thereof and in a pharmaceutically accepted carrier, adjuvant or vehicle.

Embodiments of the present invention include a pharmaceutical composition comprising a dose of about 0.1 mg/kg to 300 mg/kg of 4,4'-thiodianiline, 4,4'-diaminobenzophenone, 4,4'-methylenedianiline, 4,4'-diaminodiphenyl ether, or (3-aminophenyl)-(4-aminophenyl) amine or the equivalent of its pharmaceutically acceptable salt.

Additional advantages of the present invention will become readily apparent to those skilled in the art from this following detailed description. As will be realized, the invention is capable of other and different embodiments, and its several details are capable of modifications in various obvious respects, all without departing from the present invention.

DESCRIPTION OF THE INVENTION

The present invention relates to therapeutic bridged dianilino compounds and their pharmaceutical compositions and method of use thereof for the prevention and treatment of epilepsies, seizures, and other electroconvulsive disorders. The therapeutic compound comprises a compound having the following formula (I):

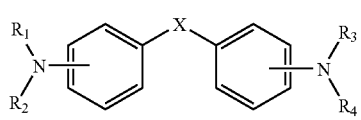

(I)

wherein $R_1$, $R_2$, $R_3$, and $R_4$, are each independently selected from the group consisting of hydrogen, hydroxy, amino, phenyl, substituted or unsubstituted $C_{1-10}$ alkyl, $C_{3-10}$ branched alkyl, substituted or unsubstituted $C_{3-8}$ cycloalkyl, substituted or unsubstituted arylalkyl (comprising Ar—$(CH_2)_n$; where Ar is aromatic and n=0-10) substituted or unsubstituted $C_{1-10}$ alkoxyl, substituted or unsubstituted $C_{1-10}$ acyl, where the substituents are, but are not limited to, substituents selected from the group consisting of halogen, phenyl, thio, amino, hydroxyl, hydroxylamino, nitrile, carboxyl, amido, phosphate, sulfate, sulfonamide, nitroso, nitrone, azido, imino, hydrazine, guanidino, oxyguanidino, methylguanidino, hydroxyguanidino, aminoguanidino, thioguanidino, amidino, oxyamidino, ureido, thioureido, thioamido, and nitro; and X is selected from the group consisting of —O—, —S—, —N(H)—, —Se—, —Si—, —CH=CH—, —C≡C—, —N=N—, —N=CH—, —CH=N—, —C(S)—, —N(H)S(O)—, —N(H)SO$_2$—, —N(H)O—, —N(H)S—, —S(O)—, —SO$_2$—, —PO$_4$—, —Si(O)—, —C(O)—, —CH$_2$—, —CF$_2$—, and a covalent bond In an embodiment of the present invention, 4,4'-thiodianiline, 4,4'-diaminobenzophenone, 4,4'-methylenedianiline, 4,4'-diaminodiphenyl ether, and (3-aminophenyl)-(4-aminophenyl) amine are formulated into a pharmaceutical preparation comprising the active agent or a pharmaceutically acceptable salt or complex thereof and a pharmaceutically acceptable carrier.

It has been discovered that the inventive compositions are useful in the prevention, palliation, and/or treatment of seizures, conduction disturbances and electroconvulsive disorders of all types and their manifestations irrespective of the origin of the ailment in a subject in need thereof including humans and other mammals. It is contemplated that the inventive compositions can be employed for preventing and/or treating other conduction disturbances of the central nervous system (CNS), and the emotional, cognitive, and motor symptoms resulting there from.

In an embodiment of the present invention, the inventive compositions are administered to a subject in need thereof to prevent or treat disturbances of the CNS, such as seizure and electroconvulsion, of either or both an acute or chronic nature, of unknown origin or secondary to conditions such as, but not limited to: surgery, irradiation, or other manipulation of the brain and/or CNS; alcohol, benzodiazepine, barbiturate or other drug or chemical withdrawal; exposure to epileptogenic drugs and/or chemicals; acute or chronic injury or trauma; stroke or cerebrovascular accident; fever; meningitis or other CNS inflammation or infection; or electroconvulsive therapy.

In practicing the present invention, the compound having formula (I) or a pharmaceutically acceptable salt or complex thereof is formulated into pharmaceutical compositions. In an embodiment of the present invention, 4,4'-thiodianiline, 4,4'-diaminobenzophenone, 4,4'-diaminodiphenyl ether, 4,4'-methylenedianiline, or (3-aminophenyl)-(4-aminophenyl) amine are formulated into pharmaceutical compositions The compound of formula (I) includes all resolved enantiomers, diastereoisomers, tautomers, salts, solvates and polymorphic forms thereof. Salt forms of 4,4'-thiodianiline, 4,4'-diaminobenzophenone, 4,4'-diaminodiphenyl ether, 4,4'-methylenedianiline, or (3-aminophenyl)-(4-aminophenyl) amine include, but are not limited to the following: inorganic acid addition salts such as hydrochloride, hydrobromide, sulfate, phosphate and nitrate; organic acid addition salts such as acetate, galactarate, propionate, succinate, lactate, glycolate, malate, tartrate, citrate, maleate, fumarate, methanesulfonate, salicylate, p-toluenesulfonate, benzenesulfonate, and ascorbate; salts with acidic amino acids such as aspartate and glutamate; the salts may in some cases by hydrates or solvates with alcohols and other solvents. Salt forms of 4,4'-thiodianiline, 4,4'-diaminobenzophenone, 4,4'-methylenedianiline, or (3-aminophenyl)-(4-aminophenyl) amine, can be prepared by mixing the acid in a conventional solvent, with or without alcohols or water.

The compounds of the present invention are useful in pharmaceutical compositions for systemic administration to mammals including humans as a single agent, or as a primary or adjunct agent with any other medication, chemical, drug or non-drug therapy, or combination thereof.

The aforementioned administration of 4,4'-thiodianiline, 4,4'-diaminobenzophenone, 4,4'-methylenedianiline, 4,4'-diaminodiphenyl ether, or (3-aminophenyl)-(4-aminophenyl) amine, or pharmaceutically acceptable salts or complexes thereof is to be employed acutely, or as a single dose, or administered intermittently, or on a regular schedule of unspecified duration, or by continuous infusion of unspecified duration, by an acceptable route of administration including, but not limited to, the oral, buccal, intranasal, pulmonary, transdermal, rectal, vaginal, intradermal, intrathecal, intravenous, intramuscular, and/or subcutaneous routes.

The pharmaceutical preparations can be employed in unit dosage forms, such as tablets, capsules, pills, powders, granules, suppositories, sterile and parenteral solutions, or suspensions, sterile and non-parenteral solutions or suspensions, oral solutions or suspensions, oil in water or water in oil emulsions and the like, containing suitable quantities of an active ingredient. Topical application can be in the form of ointments, creams, lotions, jellies, sprays, douches, and the like. For oral administration either solid or fluid unit dosage forms can be prepared with the compounds of Formula I.

Either fluid or solid unit dosage forms can be readily prepared for oral administration. For example, the compounds can be mixed with conventional ingredients such as dicalciumphosphate, magnesium aluminum silicate, magnesium stearate, calcium sulfate, starch, talc, lactose, acacia, methylcellulose and functionally similar materials as pharmaceutical excipients or carriers. A sustained release formulation may optionally be used. Capsules may be formulated by mixing the compound with a pharmaceutical diluent which is inert and inserting this mixture into a hard gelatin capsule having the appropriate size. If soft capsules are desired, a slurry (or other dispersion) of the compound, with an acceptable vegetable, light petroleum or other inert oil can be encapsulated by machine into a gelatin capsule.

Suspensions, syrups, and elixirs may be used for oral administration of fluid unit dosage forms. A fluid preparation including oil may be used for oil soluble forms. A vegetable oil, such as corn oil, peanut oil, or safflower oil, for example, together with flavoring agents, sweeteners, and any preservatives produces an acceptable fluid preparation. A surfactant may be added to water to form syrup for fluid dosages. Hydro-alcoholic pharmaceutical preparations may be used that have an acceptable sweetener, such as sugar, saccharine, or a biological sweetener and a flavoring agent in the form of an elixir.

Pharmaceutical compositions for parental and suppository administration can also be obtained using techniques standard in the art. Another preferred use of these compounds is in a transdermal parenteral pharmaceutical preparation in a mammal such as a human.

The above and other drugs can be present in the reservoir alone, or in combination form with pharmaceutical carriers. The pharmaceutical carriers acceptable for the purpose of this invention are the art known carriers that do not adversely affect the drug, the host, or the material comprising the drug delivery device. Suitable pharmaceutical carriers include sterile water, saline, dextrose, dextrose in water or saline, condensation products of castor oil and ethylene oxide combining about 30 to about 35 moles of ethylene oxide per mole of castor oil, liquid acid, lower alkanols, oils (such as corn oil, peanut oil, sesame oil and the like), with emulsifiers such as mono- or di-glyceride of a fatty acid or a phosphatide (e.g., lecithin and the like), glycols, polyalkyne glycols, aqueous media in the presence of a suspending agent (for example, sodium carboxymethylcellulose), sodium alginate, poly(vinylpyrolidone), and the like (alone or with suitable dispensing agents such as lecithin), or polyoxyethylene stearate and the like. The carrier may also contain adjuvants such as preserving, stabilizing, wetting, emulsifying agents and the like together with the penetration enhancer of this invention.

By "effective amount," "therapeutic amount," "therapeutic effective amount" or "effective dose" is meant that the amount sufficient to elicit the desired pharmacological or therapeutic effect, thus resulting in effective prevention or treatment of the condition or disorder. Thus, when treating a CNS disorder, an effective amount of compound is that amount sufficient to pass across the blood-brain barrier of the subject to interact with relevant receptor sites in the brain of the subject. Prevention of the condition or disorder is manifested by delaying the onset of the symptoms of the condition or disorder. Treatment of the condition or disorder is manifested by a decrease in the symptoms associated with the condition or disorder, or an amelioration of the recurrence of the symptoms of the condition of disorder.

The effective dose can vary, depending upon factors such as the condition of the patient, the severity of the symptoms of the disorder, age, weight, metabolic status, concurrent medications, and the manner in which the pharmaceutical composition is administered. Typically, the effective dose of compounds generally requires administering the compound in an amount of about 0.1 to 500 mg/kg of the subject's weight. In an embodiment of the present invention, a dose of about 0.1 to about 300 mg/kg is administered per day indefinitely or until symptoms associated with the condition or disorder cease. Preferably, about 1.0 to 50 mg/kg body weight is administered per day. The required dose is less when administered parenterally.

EXAMPLE 1

The Maximal Electroshock Seizure (MES) or Maximal Seizure Pattern Test

The MES is an experimental model for generalized tonic-clonic seizures that identifies compounds that prevent seizure spread. The MES model is highly reproducible and has a consistent endpoint. An advantage of this model is that the behavioral and electrographic seizures are consistent with those observed in humans [2].

In the MES test, the animal receives an electrical stimulus, 0.2 seconds in duration, via corneal electrodes primed with an electrolyte solution containing an anesthetic agent. The 0.2 second stimulation is generated with 150 mA in rats and 50 mA in mice at 60 Hz. Rats, weighing between 105 g and 130 g, and mice, weighing between 18 g and 25.5 g, receive an electrical stimulus 15 minutes, 30 minutes, 1 hour, 2 hours, and 4 hours after administration of the test compound. In rats, the compound is administered orally, while mice receive the agent via intraperitoneal injection. The test endpoint, electrogenic seizure, is manifested as hindlimb tonic extension. Inhibition of hindlimb tonic extension indicates that the test compound is able to inhibit MES-induced seizure spread and therefore may have anti-seizure activity [2-4]. The results of the MES test suggest that this class of compounds is effective in preventing seizure spread in both rats and mice (Tables 1 and 2).

TABLE 1

Percentage of mice in which 30, 100, or 300 mg/kg of the test compound prevented MES-induced seizure 0.5 or 4 hours after intraperitoneal administration.

| Test Compound | 0.5 h (%) | 4.0 h (%) |
|---|---|---|
| 4,4'-thiodianiline | | |
| 30 mg/kg | 0 | 0 |
| 100 mg/kg | 66 | 100 |
| 300 mg/kg | 100 | 100 |

TABLE 1-continued

Percentage of mice in which 30, 100, or 300 mg/kg of the test compound prevented MES-induced seizure 0.5 or 4 hours after intraperitoneal administration.

| Test Compound | 0.5 h (%) | 4.0 h (%) |
|---|---|---|
| 4,4'-methylenedianiline | | |
| 30 mg/kg | 0 | 0 |
| 100 mg/kg | 100 | 0 |
| 300 mg/kg | 100 | 100 |
| 4,4'-diaminobenzophenone | | |
| 30 mg/kg | 0 | 0 |
| 100 mg/kg | 100 | 100 |
| 300 mg/kg | 100 | 100 |
| 4,4'-diaminodiphenyl ether | | |
| 30 mg/kg | 0 | 0 |
| 100 mg/kg | 100 | 100 |
| 300 mg/kg | 100 | 100 |
| (3-aminophenyl)-(4-aminophenyl) amine | | |
| 30 mg/kg | 0 | 0 |
| 100 mg/kg | 100 | 100 |
| 300 mg/kg | 100 | 100 |

TABLE 2

Percentage of rats in which 30 mg/kg of the test compound prevented MES-induced seizure 0.25, 0.5, 1.0, 2.0 or 4.0 hours after oral administration.

| Test Compound (30 mg/kg) | 0.25 h (%) | 0.5 h (%) | 1.0 h (%) | 2.0 h (%) | 4.0 h (%) |
|---|---|---|---|---|---|
| 4,4'-thiodianiline | 100 | 100 | 100 | 100 | 100 |
| 4,4'-methylenedianiline | 100 | 75 | 92 | 100 | 50 |
| 4,4'-diaminobenzophenone | 50 | 100 | 75 | 100 | 75 |
| 4,4'-diaminodiphenyl ether | 100 | 100 | 75 | 75 | 100 |
| (3-aminophenyl)-(4-aminophenyl) amine | 0 | 50 | 75 | 50 | 50 |

A full dose-response curve was also generated in rats to determine the $ED_{50}$ value (n=8 at each time point). These experiments were conducted at the compound's time of peak pharmacodynamic activity and the results are shown in Table 3. 4,4'-Diaminodiphenyl ether was the most active compound ($ED_{50}$: 5.24±4.67 mg/kg) and also had the longest time to peak effect (6 hours). The $ED_{50}$ of 4,4'-thiodianiline was evaluated in both rats and mice. In rats, 1 hour after oral administration, 4,4'-thiodianiline had an $ED_{50}$ of 6.60±5.07 mg/kg, and 0.5 hours after intraperitoneal administration in mice it had an $ED_{50}$ of 53.42±14.92 mg/kg.

TABLE 3

$ED_{50}$ required to inhibited MES-induced seizure at the time of peak effect in rat after oral administration of the test compound

| Test Compound | Time to Peak Effect (hours) | $ED_{50}$ (mg/kg) |
|---|---|---|
| 4,4'-thiodianiline | 1 | 6.60 ± 5.07 |
| 4,4'-methylenedianiline | 1 | 10.63 ± 5.88 |
| 4,4'-diaminobenzophenone | 1 | 7.15 ± 1.89 |
| 4,4'-diaminodiphenyl ether | 6 | 5.24 ± 4.67 |
| (3-aminophenyl)-(4-aminophenyl) amine | 2 | 31.74 ± 24.42 |

EXAMPLE 2

6 Hz Kindling Model

The 6 Hz kindling model is another experimental seizure model that effectively detects compounds with anti-seizure activity. This screen is used to evaluate the ability of a compound to prevent the acquisition of focal seizures; in particular, the capacity of a compound to prevent the development of seizures induced by a low-frequency (6 Hz), long duration (three seconds) stimulus in electrode implanted rats is evaluated [5]. Several of the most promising compounds were evaluated in this screen to further characterize their anti-seizure activity.

In the 6 Hz kindling test, mice are implanted with corneal electrodes. The test compound is administered (i.p.) to the animal at 0.25, 0.5, 1, 2, or 4 hours prior seizure induction. The seizure is initiated by delivering a current (32 mA at 6 Hz for three seconds) to the animal through the corneal electrodes. The resulting psychomotor seizure is usually characterized by a minimal clonic phase followed by stereotyped, automatistic behaviors. This response is analogous to the aura of human patients with partial seizures. If the animal does not exhibit this behavior, the test compound is considered to have protected the animal and have anti-seizure properties.

The data in Table 4 clearly indicates the capacity of 4,4'-thiodianiline, 4,4'-diaminobenzophenone, and 4,4'-methylenedianiline to inhibit 6 Hz seizures. 4,4'-Thiodianiline was the most effective compound evaluated, having an $ED_{50}$ value between 30 and 80 mg/kg. At a dose of 100 mg/kg, all four of the compounds tested inhibited seizure in 100% of the animals tested 0.25, 0.5 and 1.0 hours after administration of the compound.

TABLE 4

Percentage of Mice in which Exposure to the Test Compound Prevented Seizure in the 6 Hz Test at 0.25, 0.5, 1.0, 2.0 and 4.0 Hours after intraperitoneal Administration

| Test Compound | 0.25 h (%) | 0.5 h (%) | 1.0 h (%) | 2.0 h (%) | 4.0 h (%) |
|---|---|---|---|---|---|
| 4,4'-thiodianiline | | | | | |
| 30 mg/kg | 0 | 25 | 25 | 25 | ND |
| 80 mg/kg | 100 | 100 | 100 | 75 | 0 |
| 100 mg/kg | 100 | 100 | 100 | 100 | 0 |
| 4,4'-diaminobenzophenone | | | | | |
| 30 mg/kg | 0 | 0 | 0 | ND | ND |
| 100 mg/kg | 100 | 100 | 100 | 0 | 0 |
| 4,4'-diaminodiphenyl ether | | | | | |
| 30 mg/kg | 0 | 50 | 25 | 25 | ND |
| 100 mg/kg | 100 | 100 | 100 | 100 | 0 |

TABLE 4-continued

Percentage of Mice in which Exposure to the Test Compound Prevented Seizure in the 6 Hz Test at 0.25, 0.5, 1.0, 2.0 and 4.0 Hours after intraperitoneal Administration

| Test Compound | 0.25 h (%) | 0.5 h (%) | 1.0 h (%) | 2.0 h (%) | 4.0 h (%) |
|---|---|---|---|---|---|
| 4,4'-methylenedianiline | | | | | |
| 30 mg/kg | 0 | 0 | 0 | ND | ND |
| 100 mg/kg | 100 | 100 | 100 | 0 | 0 |

EXAMPLE 3

Hippocampal Kindling Model

The hippocampal kindling model is an experimental seizure model used to simulate focal seizures. This model evaluates the capacity of a compound to affect both the expression and acquisition of focal seizures. In addition, kindled seizures provide a methodology for studying complex brain networks that may contribute to the spread and generalizations of seizures from a focus. The hippocampal kindling model has the advantage of being one of the only kindling models that can evaluate the temporal effects of an agent in a single animal [6,7]. For this assessment, bipolar electrodes are surgically implanted in the ventral hippocampus of adult male Sprague-Dawley rats (275-300 g) under ketamine-xylazine anesthesia. Following a one-week recovery period, stage five behavioral seizures are induced by stimulating the rat 12 times per day with 50 Hz, 10 s train of 1 ms biphasic 200 µA pulses delivered every 30 min for six hours on alternating days. After five stimulus days, the animal has had 60 stimulations. A drug free control period with supramaximal stimulations is used to verify the stability of a stage five generalized seizure before the anticonvulsant activity of a drug is measured.

This screen is used to measure the capacity of the drug to prevent the expression of focal seizures. During a drug trial, the afterdischarge threshold of each animal is determined by increasing the current intensity, stepwise, until the rat displays an electrographic afterdischarge lasting at least four seconds. The animal is exposed to an initial stimulation of 20 µA; the stimulation is increased in 10 µA increments every one-two minutes until an afterdischarge is recorded. After the stability of the stage five seizure is established, the drug candidate is administered to the rats via intraperitoneal injection 15 minutes after the last control stimulation. Starting with the first dose, the anticonvulsant activity of the test agent is measured every thirty minutes for four hours. Following each stimulation, Racine seizure scores and afterdischarge durations [8] are compared to control values to quantify the anti-convulsant activity of the agent. The Racine seizure scores vary from stage 1 to 5. The stages are characterized according to the following criteria: Stage 1—mouth and facial clonus, Stage 2—stage 1 and head nodding, Stage 3—stage 2 and forelimb clonus, Stage 4—stage 3 and rearing, Stage 5—stage 4 and repeated rearing and falling [8]. Since a single animal is used, each rat serves as its own control.

4,4'-Thiodianiline was used in the rat hippocampal kindled rats to screen to measure its anticonvulsant potential. Doses of 12.5, 25, 50 and 100 mg/kg were evaluated at a minimum of seven time points (n=7 for each dose and each time point). Table 5 shows the raw data from a 100 mg/kg dose of 4,4'-thiodianiline. After oral administration of the test compound stimulation, the Racine seizure scores and afterdischarge durations were measured and are shown below. The Racine seizure scores dropped from between a stage 4 and stage 5 seizure for control measurements to between a stage 1 and stage 2 seizure after treatment with 4,4'-thiodianiline.

TABLE 5

Racine Seizure Scores and Afterdischarge Durations Following Stimulation, for Rats Treated with 100 mg/kg of 4,4'-Thiodianiline.

| Time (min) | Racine Seizure Score ± SEM | Afterdischarge Duration (sec) ± SEM |
|---|---|---|
| Control | 4.86 ± 0.14 | 72.57 ± 7.20 |
| 15 | 1.43 ± 0.81* | 19.14 ± 9.58* |
| 45 | 1.29 ± 0.84* | 25.29 ± 13.71* |
| 75 | 0.71 ± 0.57* | 24.86 ± 11.43* |
| 105 | 1.29 ± 0.64* | 33.29 ± 14.17* |
| 135 | 1.57 ± 0.81* | 34.71 ± 14.35* |
| 165 | 1.57 ± 0.65* | 57.43 ± 18.17 |
| 195 | 1.57 ± 0.69* | 55.29 ± 18.19 |
| 225 | 1.86 ± 0.70* | 71.29 ± 18.99 |
| 255 | 1.86 ± 0.63* | 65.43 ± 17.91 |

*Significantly different than control

Using the data generated from each of the doses, 4,4'-thiodianiline, was found to have an $ED_{50}$ of 51.43 mg/kg. This is the dose of 4,4'-thiodianiline required to prevent the expression of focal seizures in this model. The capacity of 4,4'-thiodianiline to elevate afterdischarge threshold and decrease afterdischarge duration suggests that it possess the ability to limit focal seizure activity originating from the ventral hippocampus.

4,4'-Diaminobenzanalide and 4,4'-diaminodiphenyl ether were also evaluated in the hippocampal kindling model. While these compounds were not as effective as 4,4'-thiodianiline, they also had the capacity to block the expression of fully kindled seizures.

EXAMPLE 4

Minimal Neurotoxicity

Toxicity in mice and rats is assessed using three screens: the rotorod in mice, positional sense and gait in rats. In mice, the test compound is administered at doses of 30, and 100 mg/kg prior to evaluation in the toxicity screens. The mice are tested at 0.5 hours and 4 hours after intraperitoneal administration of the test compound. In rats, the test compound is administered at 30 mg/kg prior to the toxicity assessment. The rats are tested at 0.25, 0.5, 1, 2, and 4 hours after oral administration of the test compound. In rats, a series of doses were tested at the time to peak effect to determine the toxicity $ED_{50}$ at this timepoint.

Rotorod Test

Toxicity in mice weighing between 18 and 25.5 g is assessed using the standardized rotorod test [9]. For each compound tested, a minimum of 18 animals are evaluated for neurotoxicity. Control mice can maintain their equilibrium for an extended period of time when they are placed on a 6-rpm rotation rod. Neurologically impaired animals cannot maintain equilibrium for one minute in each of three successive trials.

Positional Sense Test

Behavioral toxicity in twenty rats weighing between 105 and 130 g is assessed by the positional sense test. In this test, one hind leg is gently lowered over the edge of a table. If the rat experiences neurological toxicity, it will not be able to quickly lift its leg quickly back to a normal position.

Gait and Stance Test

In the gait and stance test, neurotoxicity is indicated by a circular or zigzag gait after administration of the test compound. In addition, ataxia, abnormal spread of the legs, abnormal posture, tremor hyperactivity, lack of exploratory behavior, somnolence, stupor, or catalepsy can indicate neurotoxicity. This toxicity test was conducted on rats, weighing between 105 and 130 g.

The acute neurotoxicity of this class of compounds was shown to be well above the doses required for therapeutic benefit. No acute neurotoxicity was observed as measured by the rotorod test up to four hours after mice had been given 4,4'-thiodianiline, even at doses as high as 300 mg/kg. In rats, 1 hour (the time to peak effect) after oral administration of 4,4'-thiodianiline, the $ED_{50}$ for toxicity was determined to be almost 60 times greater than the $ED_{50}$ for anti-convulsant activity. Similarly, 4,4'-diaminobenzophenone was not neurotoxic to rats. None of the rats tested at any timepoints (0.25 to 24 hours after oral administration of 4,4'-diaminobenzophenone) showed acute neurotoxic effects, even at doses as high as 500 mg/kg. In contrast, the $ED_{50}$ for anti-convulsant activity for 4,4'-diaminobenzophenone in rats was 7.15 mg/kg. In mice, 4,4'-diaminobenzophenone showed no neurotoxicity at doses below 100 mg/kg. 4,4'-Diaminodiphenyl ether, 4,4'-methylenedianiline and (3-aminophenyl)-(4-aminophenyl) amine had no significant toxicity even at 100 mg/kg in mice and 250 mg/kg in rats.

These data suggest that the acute neurotoxicity levels of these compounds in mice and rats, as assessed by the rotorod test, the positional sense and the gait and stance tests, far exceed the level required for anticonvulsant activity.

REFERENCES

1. Goodman, L. S., A. Gilman, J. G. Hardman, A. G. Gilman, and L. E. Limbird, *Goodman & Gilman's the pharmacological basis of therapeutics*. 9th/ed. 1996, New York: McGraw-Hill Health Professions Division. xxi, 1905.
2. Levy, R. H., *Antiepileptic drugs*. 3rd/ed. 1989, New York: Raven Press. xxvii, 1025.
3. Levy, R. H., R. H. Mattson, and B. S. Meldrum, *Antiepileptic drugs*. 4th/ed. 1995, New York: Raven Press. xxv, 1120.
4. White, H. S., M. Johnson, H. H. Wolf, and H. J. Kupferberg. (1995) The early identification of anticonvulsant activity: role of the maximal electroshock and subcutaneous pentylenetetrazol seizure models. *Ital J Neurol Sci* 16:73-7.
5. Toman, J. E. P., G. M. Everett, and R. K. Richards. (1952) The search for new drugs against epilepsy. *Tex Rep Biol Med* 10:96-104.
6. Lothman, E. W. and J. M. Williamson. (1994) Closely spaced recurrent hippocampal seizures elicit two types of heightened epileptogenesis: a rapidly developing, transient kindling and a slowly developing, enduring kindling. *Brain Res* 649:71-84.
7. Lothman, E. W., R. A. Salerno, J. B. Perlin, and D. L. Kaiser. (1988) Screening and characterization of antiepileptic drugs with rapidly recurring hippocampal seizures in rats. *Epilepsy Res* 2:366-379.
8. Racine, R. J. (1972) Modification of seizure activity by electrical stimulation. II. Motor seizure. *Electroencephalogr Clin Neurophysiol* 32:281-94.
9. Dunham, M. S. and T. A. Miya. (1957) A note on a simple apparatus for detecting neurological deficit in rats and mice. *J Amer Pharmac Assoc Sci Edit* 46:208-209.

While the salient features have been illustrated and described with respect to particular embodiments, it should be readily apparent that modifications can be made within the spirit and scope of the invention, and it is therefore not desired to limit the invention to the exact details shown and described.

What is claimed is:

1. A method of treating and ameliorating epilepsy, seizure or electroconvulsive disorders in mammals which comprises administering a therapeutic effective amount to said mammal of the following therapeutic compound, including resolved enantiomers, diastereomers, salts, solvates and polymorphic froms thereof, having the following formula (I):

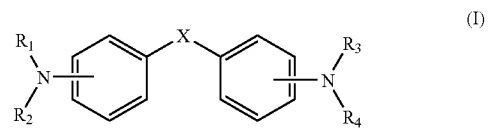

wherein $R_1$, $R_2$, $R_3$, and $R_4$, are each independently selected from the group consisting of hydrogen, hydroxy, amino, phenyl, a substituted or unsubstituted $C_{1-10}$ alkyl, $C_{3-10}$ branched alkyl, a substituted or unsubstituted $C_{3-8}$ cycloalkyl, a substituted or unsubstituted arylalkyl, a substituted or unsubstituted $C_{1-10}$ alkoxyl and a substituted or unsubstituted $C_{1-10}$ acyl; and X is selected from the group consisting of —O—, —S—, —N(H)—, —Se—, —Si—, —CH=CH—, —C≡C—, —N=N—, —N=CH—, —CH=N—, —C(S)—, —N(H)S(O)—, —N(H)SO₂—, —N(H)O—, —N(H)S—, —S(O)—, —SO₂—, —PO₄—, —Si(O)—, —C(O)—, —CH₂—, —CF₂—, and a covalent bond.

2. The method of claim 1, wherein the substituted or unsubstituted arylalkyl is Ar-(CH₂)ₙ; wherein Ar is an aromatic ring and n is from 1 to 10.

3. The method of claim 2, wherein the substituents of the substituted groups are selected from the group consisting of halogen, phenyl, thio, amino, hydroxyl, hydroxylamino, nitrile, carboxyl, amido, phosphate, sulfate, sulfonamide, nitroso, nitrone, azido, imino, hydrazine, guanidino, oxyguanidino, methylguanidino, hydroxyguanidino, aminoguanidino, thioguanidino, amidino, oxyamidino, ureido, thioureido, thioamido and nitro.

4. The method of claim 1, wherein the compound is selected form the group consisting of 4,4'-thiodianiline, 4,4'-diaminobenzophenone, 4,4'-diaminodiphenyl ether, 4,4-methylenedianiline, and (3-aminophenyl)-(4-aminophenyl) amine.

5. The method of claim 1, wherein the compound is 4,4'-thiodianiline.

6. The method of claim 1, wherein the compound is 4,4'-diaminobenzophenone.

7. The method of claim 1, wherein the compound is 4,4'-diaminodiphenyl ether.

8. The method of claim 1, wherein the compound is 4,4'-methylenedianiline.

9. The method of claim 1, wherein the compound is (3-aminophenyl)-(4-aminophenyl) amine.

10. The method of claim 1, wherein the therapeutic effective amount is from about 0.1 mg/kg to about 300 mg/kg.

11. The method of claim 1, wherein the therapeutic effective amount is from about 1 mg/kg to about 40 mg/kg.

* * * * *